United States Patent
Rudolph et al.

(10) Patent No.: US 8,702,813 B2
(45) Date of Patent: Apr. 22, 2014

(54) USE OF ASCORBIC ACID DERIVATIVES FOR DYEING KERATIN-CONTAINING FIBRES

(75) Inventors: Thomas Rudolph, Darmstadt (DE); Michaela Oberle, Rodgau (DE)

(73) Assignee: MERCK PATENT GmbH, Darmstadt (DE)

( * ) Notice: Subject to any disclaimer, the term of this patent is extended or adjusted under 35 U.S.C. 154(b) by 0 days.

(21) Appl. No.: 13/885,560

(22) PCT Filed: Oct. 19, 2011

(86) PCT No.: PCT/EP2011/005269
§ 371 (c)(1),
(2), (4) Date: May 15, 2013

(87) PCT Pub. No.: WO2012/065671
PCT Pub. Date: May 24, 2012

(65) Prior Publication Data
US 2013/0228192 A1   Sep. 5, 2013

(30) Foreign Application Priority Data
Nov. 19, 2010 (DE) .......................... 10 2010 051 725

(51) Int. Cl.
*A61Q 5/10* (2006.01)
*C07D 315/00* (2006.01)

(52) U.S. Cl.
USPC ................ 8/405; 549/207; 132/202; 132/208

(58) Field of Classification Search
USPC ................ 8/405; 549/200, 207; 132/202, 208
See application file for complete search history.

(56) References Cited

U.S. PATENT DOCUMENTS

2010/0167936 A1* 7/2010 Rudolph et al. .............. 504/299
2012/0052028 A1   3/2012 Rudolph et al.

FOREIGN PATENT DOCUMENTS

| FR | 2 939 035 | 6/2010 |
| WO | WO-2008 017346 | 2/2008 |
| WO | WO-2010 127756 | 11/2010 |

OTHER PUBLICATIONS

STIC Search Report dated Jul. 3, 2013.*
International Search Report for PCT/EP2011/005269; Date of completion of international search: May 9, 2012, Date of mailing of international search report: May 30, 2012.
Oreal, "Use of ascorbic acid acetal derivatives for dyeing human keratin fibres, preferably hair," Espacenet, Publlication Date: Jun. 4, 2010; English Abstract of FR-2 939 035.

* cited by examiner

*Primary Examiner* — Eisa Elhilo
(74) *Attorney, Agent, or Firm* — Millen, White, Zelano & Branigan, P.C.

(57) ABSTRACT

The invention relates to the use of specific ascorbic acid derivatives for dyeing keratin-containing fibers or as direct dyes for the preparation of a composition for dyeing keratin-containing fibers, and to methods for dyeing keratin-containing fibers, in particular for dyeing human hair.

15 Claims, No Drawings

USE OF ASCORBIC ACID DERIVATIVES FOR DYEING KERATIN-CONTAINING FIBRES

The invention relates to the use of specific ascorbic acid derivatives for dyeing keratin-containing fibres or as direct dyes for the preparation of a composition for dyeing keratin-containing fibres, and to methods for dyeing keratin-containing fibres, in particular for dyeing human hair.

For the dyeing of keratin-containing fibres, use is generally made of either direct dyes or oxidation dyes, which are formed by oxidative coupling of one or more developing components to one another or to one or more coupler components. Coupler and developer components are also referred to as oxidation dye precursors.

In the case of so-called oxidation dyes, described, inter alia, in "Kosmetik und Hygiene" [Cosmetics and Hygiene] by Wilfried Umbach, Wiley-VCH, 2004, a coupling component (modifier, coupler) is reacted with a developing component (oxidation base, developer) using oxidants, such as, for example, hydrogen peroxide, on or in some cases in the keratin-containing fibre to give the dye. Alkaline and oxidative conditions usually prevail here, at least during the dyeing process. The oxidative medium is necessary in order that the developing component can be oxidised and can react with the coupling component in a coupling reaction, at least to give a precursor of a dye. The alkaline medium serves firstly for the development of the oxidative action of, for example, hydrogen peroxide and secondly for opening of the fibre structure, so that the coupling component and/or the developing component and/or dyes formed therefrom or precursors thereof are able to penetrate more deeply into the fibre. The deeper the components and/or the dyes or precursors thereof penetrate into the fibre, the more durable the dyeing. Both components preferably contain unsubstituted or substituted hydroxyl or amine groups, preferably in the ortho-, and para-position in the case of the developing component and in the meta-position in the case of the coupling component. In the case of the formation of a dye of this type from the coupling component and the developing component, bonding of the dye to the fibre may additionally occur.

Under the influence of oxidants, for example hydrogen peroxide, as described above, fibre damage may occur in some cases. Furthermore, some oxidation dye precursors or certain mixtures of oxidation dye precursors can sometimes have a sensitising action in people with sensitive skin. Direct dyes are applied under more gentle conditions, but their disadvantage consists in the fact that the dyeings frequently have only inadequate fastness properties. Fastness properties are, for example, light, rubbing, perspiration and washing fastness.

In the case of the currently conventional direct dyes, the bonding ability is frequently weakly pronounced, meaning that the dye can be washed out relatively rapidly by, for example, perspiration or water. Owing to the low bonding ability of the dye to the respective fibre, the yield of the dye in the dyeing process is, in addition, low and the intensity of the dyeing may consequently be low. On use of, in particular synthetic, dyes, in particular in the human area of application, low tolerability may also be present.

Thus, there continues to be a demand for, inter alia, tolerated and in particular skin-tolerated, dyes for dyeing keratin-containing fibres which have good bonding ability of the dye molecules to the fibre, so that more durable dyeing is possible, which simultaneously have good fastness properties and achieve intense dyeings. In the case of the simultaneous application with oxidation dyes and/or oxidants, the direct dyes should have adequate stability to hydrogen peroxide or should not lose their positive fastness and dyeing properties.

Surprisingly, it has been found that the ascorbic acid derivatives of the formula I or II, as described below, are very highly suitable as direct dyes for dyeing keratin-containing fibres. The colour effects are distinguished by the fact that the colour effect is resistant to washing out and is colour-stable and produces high shine. The colour values that can be achieved enable the production of intensified blue coordinates and thus generate a modern cool colour impression.

Surprisingly, it has furthermore been observed that intensification of the colour effect after a washing operation with conventional detergents, for example a hair shampoo, may arise.

Furthermore, the ascorbic acid derivatives of the formula I or II are suitable, as described below, for stabilising the hair colour and the dye molecules additionally employed for hair dyeing. In particular, light- and oxidation-sensitive direct dye molecules can be stabilised. Stabilisation methods include, for example, both pretreatment of the hair with ascorbic acid derivatives of the formula I or II before the actual dyeing procedure, and also post-treatment with ascorbic acid derivatives of the formula I or II after the actual dyeing procedure. In particular, red, blue and black shades of the hair colour can be stabilised.

The invention therefore relates to the use of compounds of the formula I or II

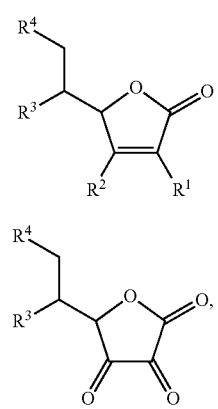

where
$R^1$ or $R^2$ each, independently of one another, denotes hydroxyl, —O-alkyl, —OC(O)-alkyl, —OPO$_3$M or O-glycosyl,
alkyl denotes a straight-chain or branched alkyl group having 1 to 10 C atoms,
M denotes alkali or alkaline-earth metal cation or H,
$R^3$ or $R^4$ each, independently of one another, stand for hydroxyl or for the formula III,

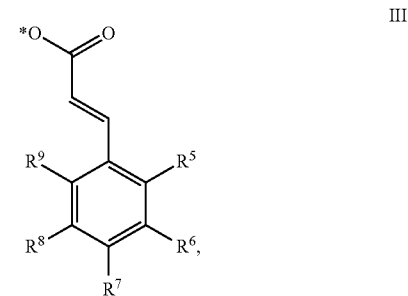

where
$R^5$ to $R^9$ each, independently of one another, denote H, —OH, straight-chain or branched alkoxy group having 1 to 20 C atoms, fluorinated straight-chain or branched alkoxy group having 1 to 20 C atoms, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X, 2H-benzotriazol-2-yl or —OC(O)-alkyl, A denotes a straight-chain or branched alkyl group having 1 to 20 C atoms and X is the counterion to the cations [NHA$_2$]$^+$ and [NA$_3$]$^+$ or the anion [SO$_3$]$^-$, with the proviso that at least one of the radicals R$^3$ or R$^4$ conforms to the formula III, and salts thereof, for dyeing keratin-containing fibres.

The invention furthermore relates to the use of compounds of the formula I or II

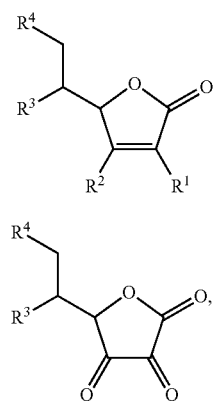

where
R$^1$ or R$^2$ each, independently of one another, denotes hydroxyl, —O-alkyl, —OC(O)-alkyl, —OPO$_3$M or O-glycosyl, alkyl denotes a straight-chain or branched alkyl group having 1 to 10 C atoms, M denotes alkali or alkaline-earth metal cation or H, R$^3$ or R$^4$ each, independently of one another, stand for hydroxyl or for the formula III,

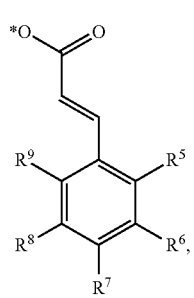

where
R$^5$ to R$^9$ each, independently of one another, denote H, —OH, straight-chain or branched alkoxy group having 1 to 20 C atoms, fluorinated straight-chain or branched alkoxy group having 1 to 20 C atoms, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X, 2H-benzotriazol-2-yl or —OC(O)-alkyl, A denotes a straight-chain or branched alkyl group having 1 to 20 C atoms and X is the counterion to the cations [NHA$_2$]$^+$ and [NA$_3$]$^+$ or the anion [SO$_3$]$^-$, with the proviso that at least one of the radicals R$^3$ or R$^4$ conforms to the formula III, and salts thereof, as direct dye for the preparation of a composition for dyeing keratin-containing fibres.

Keratin-containing fibres are preferably taken to mean human hair, wool, pelts or feathers. However, the compounds according to the invention are in principle also suitable for dyeing other natural fibres, such as, for example, cotton, jute, sisal, linen or silk, or for dyeing modified natural fibres, such as, for example, regenerated cellulose, nitro-, alkyl- or hydroxyalkyl- or acetyl-cellulose. The keratin-containing fibre is particularly preferably human hair.

The term "dyeing of keratin-containing fibres" used in accordance with the invention encompasses any form of colour change of the fibres. In particular, the colour changes covered by the terms tinting, bleaching, oxidative dyeing, semipermanent dyeing, permanent dyeing and temporary dyeing are encompassed. Likewise, colour changes may occur which have a paler colour result compared with the starting colour, such as, for example, bleaching. The term "dyeing of keratin-containing fibres" is preferably taken to mean tinting or temporary, semipermanent or permanent dyeing.

The compounds of the formula I are known, for example, from the published specifications WO 2008/017346 and/or WO 2010/127756. These published specifications relate to the use of ascorbic acid derivatives of this type as skin- and hair-bonding compounds which thereby produce permanent UV protection. The said compounds can be employed for the product protection of sensitive components in cosmetic preparations, for example of dyes or dye components in corresponding hair-dyeing compositions. Furthermore, the compounds of the formula I are capable of protecting dyed hair against a colour change. The compounds of the formula II, so-called dehydroascorbic acid derivatives, are an oxidised form of the ascorbic acid derivatives of the formula I. In the case of ascorbic acid, the following reaction, for example, applies, i.e. in the human organism the dehydroascorbic acid can be reduced back to ascorbic acid. The corresponding comments in this respect likewise apply to the compounds of the formula II.

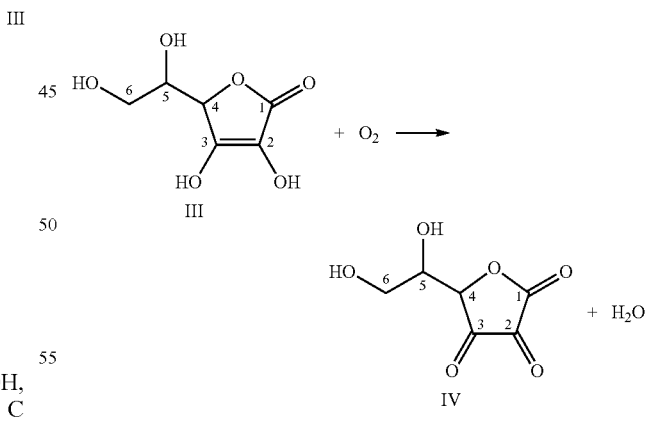

The numbering of the positions of ascorbic acid and of dehydroascorbic acid applies in the case of the following names as depicted in the above reaction scheme.

FR2939035 describes ascorbic acid acetals and the use thereof for dyeing hair.

The compounds of the formula I and II, as described above, are themselves not coloured or exhibit merely a slightly yellowish coloration. It is therefore surprising that these skin- and hair-bonding substances, besides their UV-protection action, are capable, as direct dyes, of producing colour effects on keratin-containing fibres, preferably human hair, as described above and below.

Besides the direct colour development of the compounds of the formula I or formula II, preferably of the compounds of the formula I, as described above, further advantages which may be mentioned are that these substances also produce advantageous colour effects in combination with conventional dyeing techniques, for example are suitable as coupling component for dyeing keratin-containing fibres with oxidation dyes.

In addition, the high amphiphilicity and the great water-binding capacity of the compounds of the formula I or II, as described above, means that the moisture content of a fibre treated with at least one compound of the formula I is considerably improved. This results in increased elasticity of the fibre.

With respect to human hair, the following comments, in particular, apply: the compounds of the formula I or II, and the compounds of the formula I or II indicated as preferred below, are suitable for penetrating through the hair cuticle into the hair cortex, meaning that complete and durable hair dyeing over the entire hair can be achieved. Furthermore, the compounds of the formula I or II and the compounds of the formula I or II indicated as preferred below improve the hair moisture content through excellent hydration of the hair keratin. Along with the hair moisture content, the hair structure properties, in particular the hair elasticity, are thus improved.

Compounds of the formula I or II are highly suitable for homogeneous distribution in or on keratin-containing fibres or skin, in particular on human hair, and thus formation of continuous coatings. Besides colouration homogeneity, a very pronounced homogeneous antioxidative potential can thus be generated on the fibre or the skin, which is considerably improved compared with ascorbic acid.

Since very homogeneous layer distributions can be achieved with compounds of the formula I or II, homogeneous protection properties, in particular against the undesired consequences of ultraviolet radiation, such as sunburn, photoageing or other material ageing processes, are also produced, besides homogeneous colouration. This results in a significant increase in the inherent protection time of skin and hair to harmful UV radiation after treatment with at least one compound of the formula I or II, taking into account the permanent protection aspect, with the sensitivity of skin and hair to UV radiation significantly dropping correspondingly.

The abbreviation "alkyl" denotes a straight-chain or branched alkyl group having 1 to 10 C atoms, for example having 1, 2, 3, 4, 5, 6, 7, 8, 9 or 10 C atoms, for example methyl, ethyl, isopropyl, n-propyl, isobutyl, n-butyl, tertbutyl, n-pentyl, n-hexyl, n-heptyl, n-octyl, ethylhexyl, n-nonyl or n-decyl.

Suitable alkoxy radicals for $R^1$ or $R^2$ are those whose alkyl group contains 1 to 10 C atoms, preferably 1 to 6 C atoms, particularly preferably 1 to 4 C atoms. Examples of particularly preferred alkoxy groups are methoxy, ethoxy, propoxy, isopropoxy, butoxy, isobutoxy or tert-butoxy.

The group —$OPO_3M$ is preferably the —$OPO_3H$ group, but it is also possible to employ salts of the formula I, where M in formula I corresponds to an alkali metal cation, for example of Na or K, or an alkaline-earth metal cation, for example of Mg or Ca.

The bonding of a carbohydrate in position 2 or 3 of the basic structure of ascorbic acid, referred to as O-glycosyl in formula I, can occur, for example, for monosaccharides, such as ribose, arabinose xylose, lyxose, allose, altrose, glucose, mannose, gulose, idose, galactose, talose, ribulose, xylulose, psicose, fructose, sorbose or tagatose. This list contains both isomers, i.e. in each case the D or L forms.

Preference is given to the use of glucose, galactose or fructose, very particularly preferably glucose.

In principle, however, disaccharides are also suitable, such as saccharose (or also called sucrose), lactose, trehalose, maltose, cellobiose, gentiobiose or melibiose. This list contains both the α and β forms.

From the group of the disaccharides, preference is given to the use of saccharose or lactose, particularly preferably saccharose.

Preferably, the radical $R^1$ in formula I denotes hydroxyl and $R^2$ denotes —O-alkyl, —OC(O)-alkyl, —$OPO_3M$ or O-glycosyl, as described above.

Preferably, the radical $R^2$ in formula I denotes hydroxyl and $R^1$ denotes —O-alkyl, —OC(O)-alkyl, —$OPO_3M$ or O-glycosyl, as described above.

Particularly preferably, both radicals $R^2$ and $R^1$ are hydroxyl.

$R^3$ or $R^4$ are each, independently of one another, hydroxyl or a radical of the formula III

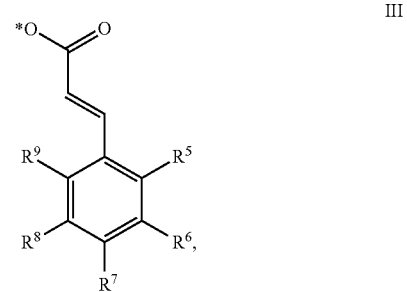

where
$R^5$ to $R^9$ each, independently of one another, denote H, —OH, straight-chain or branched alkoxy group having 1 to 20 C atoms, fluorinated straight-chain or branched alkoxy group having 1 to 20 C atoms, -A, —$NH_2$, —NHA, —$NA_2$, —NH—$(CH_2$—$CH_2$—$O)_n$—H, —N[$(CH_2$—$CH_2$—$O)_n$—H]$_2$, —[$NHA_2$]X, —[$NA_3$]X, —$SO_3H$, —[$SO_3$]X, 2H-benzotriazol-2-yl or —OC(O)-alkyl,
A denotes a straight-chain or branched alkyl group having 1 to 20 C atoms and
X is the counterion to the cations [$NHA_2$]$^+$ and [$NA_3$]$^+$ or the anion [$SO_3$]$^-$, with the proviso that at least one of the radicals $R^3$ or $R^4$ conforms to the formula III.

Particular preference is given to the 6-O-ester of ascorbic acid or of dehydroascorbic acid, i.e. preferably the radical $R^4$ stands for the formula III and $R^3$ denotes H.

The ascorbic acid skeleton or the dehydroascorbic acid skeleton here can be in the D or L form or in the form of a mixture, in particular not equimolar, of the two enantiomeric forms. L-ascorbic acid or L-dehydroascorbic acid is very particularly preferably derivatised.

In the compounds of the formula I or II, containing the moiety III, A denotes a straight-chain or branched alkyl group having 1 to 20 C atoms. A is preferably a straight-chain or branched alkyl group having 1 to 10 C atoms, as described above. A is particularly preferably a straight-chain or branched alkyl group having 1 to 4 C atoms.
n stands for an integer from 1 to 25, preferably for an integer of 1, 2, 3, 4 or 5.
X describes the counterion for the cations [$NHA_2$]$^+$ and [$NA_3$]$^+$, where A has one of the meanings indicated above, preferably Cl⁻, Br⁻, I⁻ or $[SO_4]^{2-}$ or the counterion of the anion $[SO_3]^-$, preferably an ammonium ion or an alkali metal or alkaline-earth metal cation, such as $Na^+$, $K^+$, $Mg^{2+}$ or $Ca^{2+}$.

However, it is also possible for partial charges to be compensated in the molecule itself, i.e. for compounds of the formula I to be in the form of a zwitterionic structure.

Compounds of the formula I can also be used in accordance with the invention as salts, i.e. at least one hydroxyl group of the ascorbic acid skeleton is in deprotonated form and the charge is compensated by a countercation, for example an alkali or alkaline-earth metal cation.

The substituents $R^5$ to $R^9$ in the compounds of the formula I or II are preferably each, independently of one another, H, straight-chain or branched alkoxy group having 1 to 20 C atoms, fluorinated straight-chain or branched alkoxy group having 1 to 20 C atoms or —OC(O)-alkyl, where alkyl has a meaning indicated above or indicated as preferred.

In the substituents $R^5$ to $R^9$, the straight-chain or branched alkoxy group preferably has 1 to 10 C atoms, very particularly preferably 1 to 4 C atoms.

In the substituents $R^5$ to $R^9$, the fluorinated straight-chain or branched alkoxy group preferably has 1 to 10 C atoms, very particularly preferably 1 to 4 C atoms.

At least one substituent of the substituents $R^5$ to $R^9$ is preferably a straight-chain or branched alkoxy group, as described above.

The radical $R^6$ is preferably H.

The radical $R^8$ is preferably H.

The radical $R^5$ is particularly preferably H or a straight-chain or branched alkoxy group, as described above.

The radical $R^9$ is particularly preferably H or a straight-chain or branched alkoxy group, as described above.

The radical $R^7$ is preferably a straight-chain or branched alkoxy group having 1 to 20 C atoms, a fluorinated straight-chain or branched alkoxy group having 1 to 20 C atoms or —OC(O)-alkyl, where alkyl has a meaning indicated above or indicated as preferred. The radical $R^7$ is particularly preferably a straight-chain alkoxy group having 1 to 10 C atoms, very particularly preferably 1 to 4 C atoms.

Preferred individual compounds of the formula I are the compounds 4-methoxycinnamic acid 6-O-ascorbate, 2,4-dimethoxycinnamic acid 6-O-ascorbate, 2,4,6-trimethoxycinnamic acid 6-O-ascorbate, 2,3,4-trimethoxycinnamic acid 6-O-ascorbate, 2,4,5-trimethoxycinnamic acid 6-O-ascorbate.

The compounds of the formula I or of the formula II can be prepared by processes as described in WO 2008/017346 or in WO 2010/127756. In particular, the compounds of the formula I or II are prepared by esterifications. The starting compounds required for this purpose are commercially available or can be synthesised by conventional methods. Precise reaction conditions are indicated in WO 2008/017346 on pages 35 to 42 and WO 2010/127756 on pages 9 to 13. Compounds of the formula II can be prepared by suitable oxidation from compounds of the formula I or can be generated in situ therefrom.

The compounds of the formula I or II, as described above or described as preferred, are employed, in particular, in compositions for dyeing keratin-containing fibres, in particular for dyeing human hair, which are selected, for example, from a coloured setting composition, a coloured blow-dry lotion, a coloured blow-dry foam, a coloured rinse, a coloured gel or a coloured cream. However, they may also be present in compositions for permanent hair dyeing, for example in multi-component systems.

The corresponding compositions for dyeing keratin-containing fibres, as described above, preferably comprise the compound(s) of the formula I and/or II in amounts above 0.01% by weight and below 10% by weight, in each case based on the entire composition. Preferred compositions for dyeing keratin-containing fibres are characterised in that they comprise the compound(s) of the formula I or II in amounts of 0.05 to 5% by weight, preferably 0.1 to 2.5% by weight, particularly preferably 0.25 to 1.5% by weight and in particular 0.4 to 1% by weight, in each case based on the entire composition.

The corresponding compositions comprising at least one compound of the formula I and/or of the formula II serve for changing the colour of keratin-containing fibres, as described above, in particular human hair. The colour change can take place solely owing to the compound(s) of the formula I or II, but the compositions may also additionally comprise further colour-changing substances, for example further direct dyes and/or oxidation colorants. The at least one compound of the formula I and/or of the formula II is preferably used in colorants which additionally comprise 0.001 to 5% by weight of one or more oxidation dye precursors and/or direct dyes.

The composition for dyeing keratin-containing fibres comprising at least one compound of the formula I and/or of the formula II, as described above, can be formulated as a single-component composition, as a two-component composition or as a three-component composition and used correspondingly. Separation in multicomponent systems is appropriate, in particular, where incompatibilities of the ingredients are to be expected or feared. In the case of such systems, the composition to be employed is prepared by the consumer immediately before application by mixing the components.

For example, in the case of permanent hair dyeing, a composition comprising the oxidant as first component is often used separately from the further colorant comprising, for example, the oxidation dye precursors.

For the purposes of the present invention, the term preparation or formulation is also used synonymously alongside the term composition.

The compositions may include or comprise, essentially consist of or consist of the said necessary or optional constituents. All compounds or components which can be used in the compositions are either known and commercially available or can be synthesised by known processes.

The invention furthermore relates to a method for dyeing keratin-containing fibres, in which a composition for dyeing keratin-containing fibres comprising at least one compound of the formula I and/or II, as described above or described as preferred, is applied to the keratin-containing fibre at least once daily or at least twice or a number of times successively, left on the fibre for some time, usually about 20 to 45 minutes, and subsequently rinsed out again or washed out using a shampoo.

If the method is carried out once daily, multiple application of, for example, 5 to 7 days, is advantageous in order to achieve intense dyeing results.

If the time of application of the composition comprising the at least one compound of the formula I and/or II is to be restricted to one day, it is necessary to apply the composition at least twice, preferably two to five times, to the keratin-containing fibre in order to obtain intense hair dyeing. Due to the bonding ability of the compounds of the formula I and/or II, the hair dyeing is also retained after multiple washing-out using shampoo. It has even been found that multiple washing using a shampoo results in a further intensification of the hair dyeing.

In a preferred embodiment of the method, as described above, the rinsing-out or washing using shampoo is repeated, i.e. at least twice successively. The washing with shampoo is preferably carried out five times. The effect becomes particularly clear with the shampoo as described in Example 1, i.e. with the constituents as described in Example 1.

The method according to the invention for dyeing keratin-containing fibres described in this way is very mild, since it is possible to omit alkalising pretreatment agents.

However, it is also possible to carry out a pretreatment of the keratin-containing fibres and then to apply the composition comprising the at least one compound of the formula I and/or II.

Accordingly, the invention furthermore relates to a method for dyeing keratin-containing fibres, in which a composition for dyeing keratin-containing fibres comprising at least one compound of the formula I and/or II, as described above or described as preferred, is applied to the keratin-containing fibre pretreated by means of a pretreatment agent, left on the fibre for some time, usually about 20 to 45 minutes, and subsequently rinsed out again or washed out using a shampoo.

In a preferred embodiment of the method, as described above, the rinsing-out or washing with shampoo is repeated, i.e. at least twice successively. The washing with shampoo is preferably carried out five times. The effect becomes particularly clear with the shampoo as described in Example 1, i.e. with the constituents as described in Example 1.

A pretreatment agent of this type may be basic, acidic or neutral, but in the method according to the invention is preferably basic. The pretreatment agent preferably comprises $NH_3$ and/or $(NH_4)CO_3$. The pretreatment step is usually carried out before the dyeing step, but simultaneous performance of pretreatment step and dyeing step in the case of a corresponding formulation is also conceivable.

The corresponding compositions for dyeing comprising at least one compound of the formula I and/or II are prepared by mixing, in particular dispersing and/or emulsifying and/or dissolving, at least one compound of the formula I and/or II, as described above, with at least one vehicle which is suitable for cosmetic, pharmaceutical, dermatological preparations or household products and optionally assistants and/or fillers.

Furthermore, in order, for example, to be able to carry out further colour adaptations, the compositions comprising the at least one compound of the formula I and/or II may comprise further oxidation dye components.

Coupler components generally allow at least one substitution of a chemical radical of the coupler by the oxidised form of the developer component. A covalent bond forms here between coupler and developer component.

Couplers are preferably cyclic compounds which carry at least two groups on the ring, selected from (i) optionally substituted amino groups and/or (ii) hydroxyl groups. These groups are in conjugation through a double-bond system. If the cyclic compound is a six-membered ring, the said groups are preferably located in the ortho-position or meta-position to one another.

Developer components and coupler components are generally employed here in approximately molar amounts to one another. If the molar use has also proven advantageous, a certain excess of individual oxidation dye precursors is not disadvantageous, meaning that developer components and coupler components can be in a molar ratio of 1:0.5 to 1:3, in particular 1:1 to 1:2.

Suitable oxidation dye components of the developer type are p-phenylenediamine and derivatives thereof. Suitable p-phenylenediamines are selected from one or more compounds from the group formed by p-phenylenediamine, p-tolylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(2-hydroxyethyl)-p-phenylenediamine, 4-N,N-bis-(2-hydroxyethyl)amino-2-methylaniline, 4-N,N-bis-(2-hydroxyethyl)amino-2-chloroaniline, 2-(2-hydroxyethyl)-p-phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylene-diamine, N,N-dimethyl-3-methyl-p-phenylenediamine, N-ethyl-N-2-hydroxy-ethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylene-diamine, 2-(2-acetylaminoethyloxy)-p-phenylenediamine, N-(2-methoxy-ethyl)-p-phenylenediamine, N-(4-amino-3-methylphenyl)-N-[3-(1H-imidazol-1-yl)propyl]amine, 5,8-diaminobenzo-1,4-dioxane and physiologically tolerated salts thereof. Further suitable p-phenylenediamine derivatives are selected from at least one compound from the group p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylene-diamine, N-(4-amino-3-methylphenyl)-N-[3-(1H-imidazol-1-yl)propyl]amine, 2-methoxymethyl-p-phenylenediamine and the physiologically tolerated salts of these compounds.

Further suitable developer components which can be employed are compounds which contain at least two aromatic rings which are substituted by amino and/or hydroxyl groups. Further suitable developer components are selected, in particular, from at least one compound from the group formed by N,N'-bis-(2-hydroxyethyl)-N,N'-bis-(4'-aminophenyl)-1,3-diaminopropan-2-ol, N,N'-bis-(2-hydroxyethyl)-N,N'-bis-(4'-aminophenyl)ethylenediamine, N,N'-bis-(4'-aminophenyl)tetramethylenediamine, N,N'-bis-(2-hydroxyethyl)-N,N'-bis-(4'-aminophenyl)tetramethylenediamine, N,N'-bis-(4-(methylamino)phenyl)tetramethylenediamine, N,N'-diethyl-N,N'-bis-(4'-amino-3'-methylphenyl) ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl)piperazine, N-(4'-aminophenyl)-p-phenylenediamine and 1,10-bis-(2',5'-diaminophenyl)-1,4,7,10-tetraoxadecane and physiologically tolerated salts thereof. Further suitable bicyclic developer components are selected from N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane or one of the physiologically tolerated salts of these compounds.

It may furthermore be possible to employ a p-aminophenol derivative or one of its physiologically tolerated salts as developer component. Preferred p-aminophenols are p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(2-hydroxyethoxy)-phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)phenol, 4-amino-2-(1,2-dihydroxyethyl)phenol, 4-amino-2-fluorophenol, 4-amino-2-chlorophenol, 4-amino-2,6-dichlorophenol, 4-amino-2-(diethylaminomethyl)phenol and physiologically tolerated salts thereof. Particularly preferred compounds are p-aminophenol, 4-amino-3-methylphenol, 4-amino-2-aminomethylphenol, 4-amino-2-(1,2-dihydroxyethyl)phenol and 4-amino-2-(diethylaminomethyl)phenol.

Furthermore, the developer component can be selected from o-aminophenol and derivatives thereof, such as, for example, 2-amino-4-methylphenol, 2-amino-5-methylphenol or 2-amino-4-chlorophenol.

Furthermore, the developer component can be selected from heterocyclic developer components, such as, for example, from pyrimidine derivatives, pyrazole derivatives, pyrazolopyrimidine derivatives or physiologically tolerated salts thereof. Preferred pyrimidine derivatives are, in particular, the compounds 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine. Further suitable pyrazole derivatives are the compounds selected from 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, and physiologically tolerated salts thereof, but in particular 4,5-diamino-1-(2-hydroxyethyl)pyrazole. Suitable pyrazolopyrimidines are, in particular, pyrazolo[1,5-a]pyrimidines, where preferred pyrazolo[1,5-a]-pyrimidines are selected from pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo-[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 3-amino-7-dimethylamino-2,5-dimethylpyrazolo[1,5-a]pyrimidine and physiologically tolerated salts thereof and tautomeric forms thereof.

Further suitable developer components are selected from at least one compound from the group formed by p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, and the physiologically tolerated salts of these compounds. Further suitable developer components here are p-tolylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole and physiologically tolerated salts thereof.

The developer components are preferably used in an amount of 0.0001 to 10% by weight, preferably 0.001 to 5% by weight, in each case based on the entire colorant.

Suitable oxidation dye components of the coupler type are preferably selected from m-aminophenol and/or derivatives thereof, m-diamino-benzene and/or derivatives thereof, o-diaminobenzene and/or derivatives thereof, o-aminophenol and/or derivatives thereof, naphthalene derivatives containing at least one hydroxyl group, di- or trihydroxybenzene and/or derivatives thereof, pyridine derivatives, pyrimidine derivatives, monohydroxyindole derivatives and/or monoaminoindole derivatives, monohydroxyindoline derivatives and/or monoaminoindoline derivatives, pyrazolone derivatives, such as, for example, 1-phenyl-3-methylpyrazol-5-one, morpholine derivatives, such as, for example, 6-hydroxybenzomorpholine or 6-aminobenzomorpholine, quinoxaline derivatives, such as, for example, 6-methyl-1,2,3,4-tetrahydroquinoxaline, and/or mixtures of two or more compounds from one or more of these classes.

Further coupler components which can be used, such as m-aminophenols or derivatives thereof, are preferably selected from at least one compound from the group formed by 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamitio)benzene, 3-ethylamino-4-methylphenol, 2,4-dichloro-3-aminophenol and physiologically tolerated salts thereof.

Further coupler components which can be used, such as, for example, 3-diaminobenzenes or derivatives thereof, are preferably selected from at least one compound from the group formed by m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenyl-amine, 1-amino-3-bis-(2'-hydroxyethyl)aminobenzene and physiologically tolerated salts thereof.

Further coupler components which can be used, such as, for example, o-diaminobenzenes or derivatives thereof, are preferably selected from at least one compound from the group formed by 3,4-diaminobenzoic acid and 2,3-diamino-1-methylbenzene and physiologically tolerated salts thereof. Further coupler components which can be used, such as, for example, di- or trihydroxybenzenes and derivatives thereof, are selected from at least one compound from the group formed by resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene.

Further coupler components which can be used, such as, for example, pyridine derivatives, are selected from at least one compound from the group formed by 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine and physiologically tolerated salts thereof.

Naphthalene derivatives containing at least one hydroxyl group which are suitable as coupler component are selected from at least one compound from the group formed by 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene.

Indole derivatives which are suitable as coupler component are selected from 4-hydroxyindole, 6-hydroxyindole and 7-hydroxyindole and physiologically tolerated salts thereof.

Indoline derivatives which are suitable as coupler component are preferably selected from 4-hydroxyindoline, 6-hydroxyindoline and 7-hydroxyindoline and physiologically tolerated salts thereof.

Pyrimidine derivatives which are suitable as coupler component are selected from at least one compound from the group formed by 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and physiologically tolerated salts thereof.

Suitable coupler components are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}-amino)ethanol, 2-({3-[(2-hydroxyethyl)amino]-2-methoxy-5-methylphenyl}-amino)ethanol, 2-({3-[(2-hydroxyethyl)amino]-4,5-dimethylphenyl}amino)-ethanol, 2-[3-morpholin-4-ylphenyl)amino]ethanol, 3-amino-4-(2-methoxy-ethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or physiologically tolerated salts thereof. Particular preference is given here to resorcinol, 2-methylresorcinol, 5-amino-2-methylphenol, 3-aminophenol, 2-(2,4-diaminophenoxy)ethanol, 1,3-bis-(2,4-diaminophenoxy)propane, 1-methoxy-2-amino-4-(2'-hydroxyethylamino)-benzene, 2-amino-3-hydroxypyridine and 1-naphthol and one of the physiologically tolerated salts thereof.

The coupler components are preferably used in an amount of 0.0001 to 10% by weight, preferably 0.001 to 5% by weight, in each case based on the entire composition.

For temporary dyeings, use is usually made of colorants or tinting compositions which comprise so-called direct dyes as dyeing component. These are dye molecules which are adsorbed directly onto the substrate and do not require an oxidative process for the formation of the colour. These dyes include, for example, henna, which has been known from antiquity for colouring the body and hair. These dyeings are generally significantly more sensitive to shampooing than oxidative dyeings, with the consequence that a change of shade, which is frequently undesired, or even a visible homogeneous colour loss then occurs very much more quickly.

Furthermore, the compositions according to the invention may comprise at least one further direct dye. These are dyes which are adsorbed directly onto the hair and do not require an oxidative process for the formation of the colour. Direct dyes are usually nitrophenylenediamines, nitroaminophenols, azo dyes, anthraquinones or indophenols.

The direct dyes are in each case preferably employed in an amount of 0.001 to 20% by weight, based on the entire preparation. The total amount of direct dyes is preferably at most 20% by weight.

Direct dyes can be divided into anionic, cationic and nonionic direct dyes.

Preferred anionic direct dyes are the compounds known under the international names (INCI) or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred cationic direct dyes here are (a) cationic triphenylmethane dyes, such as, for example, Basic Blue 7, Basic Blue 26, Basic Violet 2 and Basic Violet 14, (b) aromatic systems which are substituted by a quaternary nitrogen group, such as, for example, Basic Yellow 57, Basic Red 76, Basic Blue 99, Basic Brown 16 and Basic Brown 17, and (c) direct dyes which contain a heterocycle which contains at least one quaternary nitrogen atom, as mentioned, for example, in Claims 6 to 11 of EP-A2-998 908, which is explicitly incorporated herein by way of reference.

Suitable nonionic direct dyes are, in particular, nonionic nitro and quinone dyes and neutral azo dyes.

The direct dyes employed can furthermore also be naturally occurring dyes, as are present, for example, in red henna, neutral henna, black henna, camomile blossom, sandalwood, black tea, alder buckthorn bark, sage, logwood, madder root, catechu, sedre and alkanet root.

A further possibility for changing the colour is offered by the use of colorants which comprise so-called oxo dye precursors. A first class of oxo dye precursors are compounds containing at least one reactive carbonyl group. This first class is known as component (Oxo1). A second class of oxo dye precursors is formed by CH-acidic compounds and compounds containing a primary or secondary amino group or hydroxyl group, which in turn are selected from compounds from the group formed by primary or secondary aromatic amines, nitrogen-containing heterocyclic compounds and aromatic hydroxyl compounds. This second class is known as component (Oxo2). The above-mentioned components (Oxo1) and (Oxo2) are generally not themselves dyes, and are therefore each taken individually alone not suitable for dyeing keratin-containing fibres. In combination, they form dyes in a non-oxidative process, so-called oxo dyeing. The resultant dyeings in some cases have colour fastnesses on the keratin-containing fibre which are comparable with those of oxidation dyeing.

The oxo dye precursors used are preferably a combination of
 at least one compound which contains at least one reactive carbonyl group (component (Oxo1))
with at least one compound (component Oxo2)
 compounds selected from
(Oxo2a) CH-acidic compounds
and/or from
(Oxo2b) compounds containing a primary or secondary amino group or hydroxyl group, selected from at least one compound from the group formed by primary or secondary aromatic amines, nitrogen-containing heterocyclic compounds and aromatic hydroxyl compounds.

Reactive carbonyl compounds as component (Oxo1) in the sense of the invention contain at least one carbonyl group as reactive group which reacts with component (Oxo2) with formation of a covalent bond. Preferred reactive carbonyl compounds are selected from compounds which carry at least one formyl group and/or at least one keto group, in particular at least one formyl group. Use can furthermore also be made in accordance with the invention as component (Oxo1) of compounds in which the reactive carbonyl group has been derivatised or masked in such a way that the reactivity of the carbon atom of the derivatised carbonyl group with component (Oxo2) is still present. These derivatives are preferably addition compounds
a) of amines and derivatives thereof with formation of imines or oximes as addition compound
b) of alcohols with formation of acetals or ketals as addition compound
c) of water with formation of hydrates as addition compound (component (Oxo1) is in this case c) derived from an aldehyde) onto the carbon atom of the carbonyl group of the reactive carbonyl compound.

The reactive carbonyl component used for the purposes of oxo dyeing is very particularly preferably benzaldehyde and/or cinnamaldehyde and/or naphthaldehyde and/or at least one derivative of these above-mentioned aldehydes, which carry, in particular, one or more hydroxyl, alkoxy or amino substituents.

CH-acidic compounds are generally regarded as being compounds which carry a hydrogen atom bonded to an aliphatic carbon atom, where, owing to electron-withdrawing substituents, the corresponding carbon-hydrogen bond is activated. In principle, the choice of CH-acidic compounds is unlimited, so long as a compound which is visibly coloured to the human eye is obtained after condensation with the reactive carbonyl compounds of component (Oxo1). In accordance with the invention, these are preferably CH-acidic compounds which contain an aromatic and/or heterocyclic radical. The heterocyclic radical may in turn be aliphatic or aromatic. The CH-acidic compounds are particularly preferably selected from heterocyclic compounds, in particular cationic, heterocyclic compounds.

The CH-acidic compounds of the oxo dye precursors of component (Oxo2a) are very particularly preferably selected from at least one compound from the group consisting of 2-(2-furoyl)acetonitrile, 2-(5-bromo-2-furoyl)acetonitrile, 2-(5-methyl-2-trifluoromethyl-3-furoyl)acetonitrile, 3-(2,5-dimethyl-3-furyl)-3-oxopropanitrile, 2-(2-thenoyl)acetonitrile, 2-(3-thenoyl)acetonitrile, 2-(5-fluoro-2-thenoyl)acetonitrile, 2-(5-chloro-2-thenoyl)acetonitrile, 2-(5-bro-2-thenoyl)acetonitrile, 2-(2,5-dimethylpyrrol-3-oyl) acetonitrile, 1H-benzimidazol-2-ylacetonitrile, 1H-benzothiazol-1-ylacetonitrile, 2-(pyrid-2-yl)acetonitrile, 2,6-bis(cyanomethyl)pyridine, 2-(indol-3-oyl)-acetonitrile, 8-canacetyl-7-methoxy-4-methylcoumarin, 2-(quinoxalin-2-yl)-acetonitrile, 1,2,3,3-tetramethyl-3H-indolium iodide, 1,2,3,3-tetramethyl-3H-indolium methanesulfonate, 2,3-dimethylbenzothiazolium iodide, 1,2-dihydro1,3-diethyl-4,6-dimethyl-2-oxopyrimidinium hydrogensulfate, 1,2-dihydro-1,3,4,6-tetramethyl-2-thioxopyrimidinium chloride, 1,2-dihydro-1,3-diethyl-4-methyl-2-thioxopyrimidinium hydrogensulfate, 1,2-dihydro-1,3-dipropyl-4-methyl-2-thioxopyrimidinium chloride and 1,2-dihydro-1,3-dipropyl-4-methyl-2-thioxopyrimidinium hydrogensulfate.

Furthermore, component (Oxo2b) used can be at least one oxidation dye precursor containing at least one primary or secondary amino group and/or at least one hydroxyl group. Preferably suitable representatives are given under the explanation of the oxidation dye precursors. However, it is preferred in accordance with the invention for the compounds of component (Oxo2) to be selected only from CH-acidic compounds.

The above-mentioned compounds of component (Oxo1) and component (Oxo2) are, if they are used, in each case preferably used in an amount of 0.03 to 65 mmol, in particular 1 to 40 mmol, based on 100 g of the entire composition.

The compositions particularly preferably additionally comprise hydrogen peroxide. Compositions of this type for dyeing and optionally simultaneously lightening keratin-containing fibres are particularly preferably those which comprise 0.5 to 15% by weight, preferably 1 to 12.5% by weight, particularly preferably 2.5 to 10% by weight and in particular 3 to 6% by weight of hydrogen peroxide (calculated as 100% $H_2O_2$).

The hydrogen peroxide can also be employed in the form of addition compounds thereof onto solid supports, preferably hydrogen peroxide itself is used. The hydrogen peroxide is employed as a solution or in the form of a solid addition compound of hydrogen peroxide onto inorganic or organic compounds, such as, for example, sodium perborate, sodium percarbonate, magnesium percarbonate, sodium percarbamide, polyvinylpyrrolidone $nH_2O_2$ (n is a positive integer greater than 0), urea peroxide and melamine peroxide.

Very particular preference is given to aqueous hydrogen peroxide solutions. The concentration of a hydrogen peroxide solution is determined on the one hand by the legal specifications and on the other hand by the desired effect; 6 to 12 percent solutions in water are preferably used.

For a colour change by means of lightening or bleaching of the substrate, for example the hair, at least one bleach enhancer is preferably additionally employed in cosmetic compositions besides the oxidants.

Bleach enhancers are preferably employed in order to increase the bleaching action of the oxidant, in particular the hydrogen peroxide. Suitable bleach enhancers are
(BV-i) compounds which give rise to aliphatic peroxocarboxylic acids and/or optionally substituted perbenzoic acid under perhydrolysis conditions,
and/or
(BV-ii) carbonate salts and/or hydrogencarbonate salts,
and/or
(BV-iii) organic carbonates,
and/or
(BV-iv) carboxylic acids,
and/or
(BV-v) peroxo compounds.

Bleach enhancers are preferably peroxo compounds, in particular inorganic peroxo compounds. The bleach-enhancing peroxo compounds do not include any addition products of hydrogen peroxide onto other components nor hydrogen peroxide itself. In addition, the choice of peroxo compounds is not subject to any restrictions. Preferred peroxo compounds are peroxydisulfate salts, persulfate salts, peroxydiphosphate salts (in particular ammonium peroxydisulfate, potassium peroxydisulfate, sodium peroxydisulfate, ammonium persulfate, potassium persulfate, sodium persulfate, potassium peroxydiphosphate) and peroxides (such as barium peroxide and magnesium peroxide). Of these peroxo compounds, which can also be employed in combination, preference is given in accordance with the invention to the peroxydisulfates, in particular ammonium peroxydisulfate. Preference is given here to compositions for dyeing and optionally simultaneously lightening keratinic fibres which additionally comprise 0.01 to 2% by weight of at least one solid peroxo compound, which is selected from ammonium, alkali-metal and alkaline-earth metal persulfates, peroxomonosulfates and peroxydisulfates, where preferred compositions comprise peroxydisulfates, which are preferably selected from sodium peroxydisulfate and/or potassium peroxydisulfate and/or ammonium peroxydisulfate, and where preferred compositions comprise at least two different peroxydisulfates.

Particular preference is furthermore given to persulfates, in particular the mixture of potassium peroxosulfate, potassium hydrogensulfate and potassium sulfate known as Caro's salt.

The bleach enhancers are preferably present in the cosmetic compositions according to the invention in amounts of 5 to 30% by weight, in particular in amounts of 8 to 20% by weight, in each case based on the weight of the ready-to-use composition.

Furthermore, it has proven advantageous for the colorants and/or lightening compositions to comprise nonionogenic surface-active substances.

Preference is given here to surface-active substances which have an HLB value of 5.0 or greater. For the definition of the HLB value, reference is expressly made to the comments in Hugo Janistyn, Handbuch der Kosmetika und Riechstoffe [Handbook of Cosmetics and Fragrances], Volume II: Die Körperpflegemittel [Body-Care Compositions], 2nd Edition, Dr Alfred Hüthig Verlag Heidelberg, 1973, pages 68-78 and Hugo Janistyn, Taschenbuch der modernen Parfümerie und Kosmetik [Pocketbook of Modern Perfumery and Cosmetics], 4th Edition, Wissenschaftliche Verlagsgesellschaft m.b.H. Stuttgart, 1974, pages 466-474, and the original papers cited therein.

Owing to the simple processability, particularly preferred nonionogenic surface-active substances here are substances which are commercially available in pure form as solids or liquids. The definition of purity in this connection does not relate to chemically pure compounds. Instead, in particular in the case of natural products, it is possible to employ mixtures of different homologues, for example having different alkyl chain lengths, as are obtained in the case of products based on natural fats and oils. Also in the case of alkoxylated products, mixtures of different degrees of alkoxylation are usually present. The term purity in this connection instead relates to the fact that the substances selected should preferably be free from solvents, extenders and other accompanying substances.

As further constituent, the compositions according to the invention may comprise at least one ammonium compound from the group ammonium chloride, ammonium carbonate, ammonium bicarbonate, ammonium sulfate and/or ammonium carbamate in an amount of 0.5 to 10, preferably 1 to 5% by weight, based on the entire composition.

Furthermore, the colorants and/or lightening compositions according to the invention may comprise further active compounds, assistants and additives, such as, for example, nonionic polymers, such as, for example, vinylpyrrolidone-vinyl acrylate copolymers, poyvinylpyrrolidone and vinylpyrrolidone-vinyl acetate copolymers and polysiloxanes, cationic polymers, such as quaternised cellulose ethers, polysiloxanes containing quaternary groups, dimethyldiallylammonium chloride polymers, acrylamide-dimethyldiallylammonium chloride copolymers, diethyl sulfate-quaternised dimethylaminoethyl methacrylate-vinylpyrrolidone copolymers, vinylpyrrolidone-imidazolinium methochloride copolymers and quaternised polyvinyl alcohol, zwitterionic and amphoteric polymers, such as, for example, acrylamidopropyltrimethylammonium chloride-acrylate copolymers and octylacrylamide-methyl methacrylate-tert-butylaminoethyl methacrylate-2-hydroxypropyl methacrylate copolymers, anionic polymers, such as, for example, polyacrylic acids, crosslinked polyacrylic acids, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and acrylic acid-ethyl acrylate-N-tert-butylacrylamide terpolymers, thickeners, such as agar-agar, guar gum, alginates, xanthan gum, gum arabic, karaya gum, carob seed flour, linseed gums, dextrans, cellulose derivatives, for example methylcellulose, hydroxyalkylcellulose and carboxymethylcellulose, starch fractions and derivatives, such as amylose, amylopectin and dextrins, clays, such as, for example, bentonite or fully synthetic hydrocolloids, such as, for example, polyvinyl alcohol, structurants, such as maleic acid and lactic acid, hair-conditioning compounds, such as phospholipids, for example soya lecithin, egg lecitin and cephalins, protein hydrolysates, in particular elastin, collagen, keratin, milk protein, soya protein and wheat protein hydrolysates, condensation products thereof with fatty acids and quaternised protein hydrolysates, perfume oils, dimethylisosorbide and cyclodextrins, solvents and solubilisers, such as ethanol, isopropanol, ethylene glycol, propylene glycol, propylene glycol, glycerol and diethylene glycol, fibre structure-improving active compounds, in particular mono-, di- and oligosaccharides, such as, for example, glucose, galactose, fructose, fruit sugar and lactose, quaternised amines, such as methyl-1-alkylamidoethyl-2-alkylimidazolinium methosulfate antifoams, such as silicones, dyes for tinting the composition, antidandruff active compounds, such as Piroctone Olamine, Zink Omadine and climbazole, light-protection agents, in particular derivatised benzophenones, cinnamic acid derivatives and triazines, substances for adjusting the pH, such as, for example, conventional acids, in particular edible acids and bases, active compounds, such as panthenol, pantothenic acid, allantoin, pyrrolidonecarboxylic acids and salts thereof, as well as bisabolol, vitamins, provitamins and vitamin precursors, in particular those from groups A, $B_3$, $B_5$, $B_6$, C, E, F and H, plant extracts, such as the extracts from green tea, oak bark, stinging nettles, witch hazel, hops, camomile, burdock root, horsetail, hawthorn, linden blossom, almonds, aloe vera, spruce needles, horse chestnut, sandalwood, juniper, coconut, mango, apricot, lime, wheat, kiwi, melon, orange, grapefruit, sage, rosemary, birch, mallow, cuckoo flower, wild thyme, yarrow, thyme, lemon balm, restharrow, coltsfoot, marshmallow, meristem, ginseng and ginger root, cholesterol, consistency modifiers, such as sugar esters, polyol esters or polyalkyl ethers, fats and waxes, such as spermaceti, beeswax, montan wax and paraffins, fatty alcohols and fatty acid esters, fatty acid alkanolamides, complexing agents, such as EDTA, NTA, β-alaninediacetic acid and phosphonic acids, swelling and penetration substances, such as glycerol, propylene glycol monoethyl ether, carbonates, hydrogencarbonates, guanidines, ureas and primary, secondary and tertiary phosphates, opacifiers, such as latex, styrene-PVP and styrene-acrylamide copolymers pearlescent agents, such as ethylene glycol mono- and distearate and PEG-3 distearate, pigments, stabilisers for hydrogen peroxide and other oxidants, blowing agents, such as propane/butane mixtures, $N_2O$, dimethyl ether, $CO_2$ and air, antioxidants.

With respect to further optional components and the amounts of these components employed, express reference is made to the relevant handbooks known to the person skilled in the art, for example Kh. Schrader, Grundlagen und Rezepturen der Kosmetika [Principles and Recipes of Cosmetics], 2nd Edition, Huthig Buch Verlag, Heidelberg, 1989.

The compositions according to the invention can contain the ingredients in a suitable aqueous, alcoholic or aqueous/alcoholic vehicle. For the purposes of hair dyeing, vehicles of this type are, for example, creams, emulsions, gels or also surfactant-containing foaming solutions, such as, for example, shampoos, foam aerosols or other preparations which are suitable for application to the hair. However, it is also possible to prepare a pulverulent or also tablet-form formulation, which is preferred for colorants and/or lightening compositions.

Aqueous/alcoholic solutions are taken to mean, for example, aqueous solutions comprising 3 to 70% by weight of a $C_1$-$C_4$ alcohol, in particular ethanol or isopropanol. Aqueous/alcoholic solutions of this type may additionally comprise further organic solvents, such as, for example, methoxybutanol, benzyl alcohol, ethyl diglycol or 1,2-propylene glycol. Preference is given here to all water-soluble organic solvents.

Preferred compositions are characterised in that they additionally comprise a non-aqueous solvent, where particularly preferred compositions comprise the solvent in a concentration of 0.1-30 percent by weight, preferably in a concentration of 1-20 percent by weight, very particularly preferably in a concentration of 2-10 percent by weight, in each case based on the composition.

In further preferred compositions, the solvent is selected from ethanol, n-propanol, isoporanol, n-butanol, propylene glycol, n-butylene glycol, glycerol, diethylene glycol monoethyl ether, diethylene glycol mono-n-butyl ether, phenoxyethanol and benzyl alcohol and mixtures thereof.

The pH of the compositions according to the invention can be adjusted in a broad range through suitable ingredients, such as acidifying agents or alkalising agents.

Oxidative dyeing of keratin-containing fibres can in principle be carried out with atmospheric oxygen in the presence of oxidation dye precursors. However, preference is given to the use of a chemical oxidant. Suitable oxidants are persulfates, chlorites and in particular hydrogen peroxide or addition products thereof, as described above.

In addition, the compositions may comprise metal ions or metal ion complexes, for example Cu, Fe, Mn or Ru ions or complexes of these ions. Furthermore, the presence of complexing agents is advantageous in the case of addition of these metal ions. The complexing agents here can be selected from polycarboxylic acids, geminal diphosphonic acids, aminophosphonic acids, phosphonopolycarboxylic acids, cyclodextrins, aminodicarboxylic acids, polyacetals or phosphonates.

The compositions are preferably formulated to be low-water or water-free. Preferred compositions are characterised in that they comprise less than 5% by weight, preferably less than 2% by weight, particularly preferably less than 1% by weight and in particular less than 0.5% by weight of water. The water content of the compositions can be determined, for example, by means of Karl Fischer titration.

The ascorbic acid derivatives of the formula Ia and IIa,

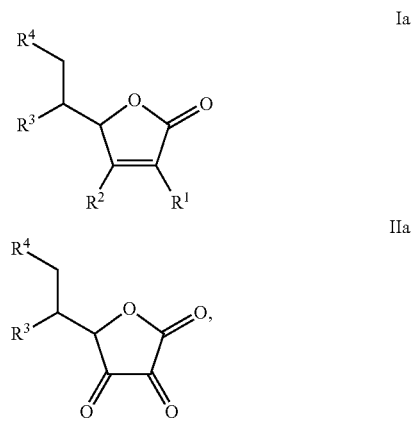

where $R^1$ or $R^2$ each, independently of one another, denotes hydroxyl, —O-alkyl, —OC(O)-alkyl, —OPO$_3$M or O-glycosyl, alkyl denotes a straight-chain or branched alkyl group having 1 to 10 C atoms, M denotes alkali or alkaline-earth metal cation or H, $R^3$ or $R^4$ each, independently of one another, stands for hydroxyl or for the formula IV, V, VI, VII, VIII, IX, X, XI or XII,

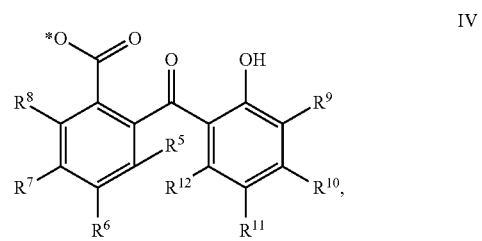

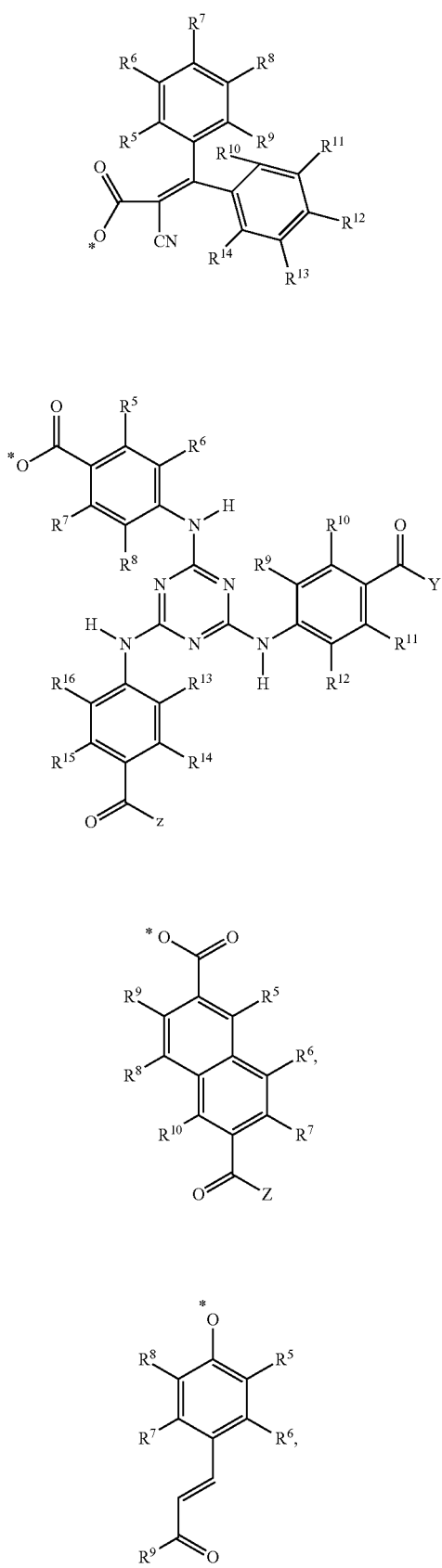
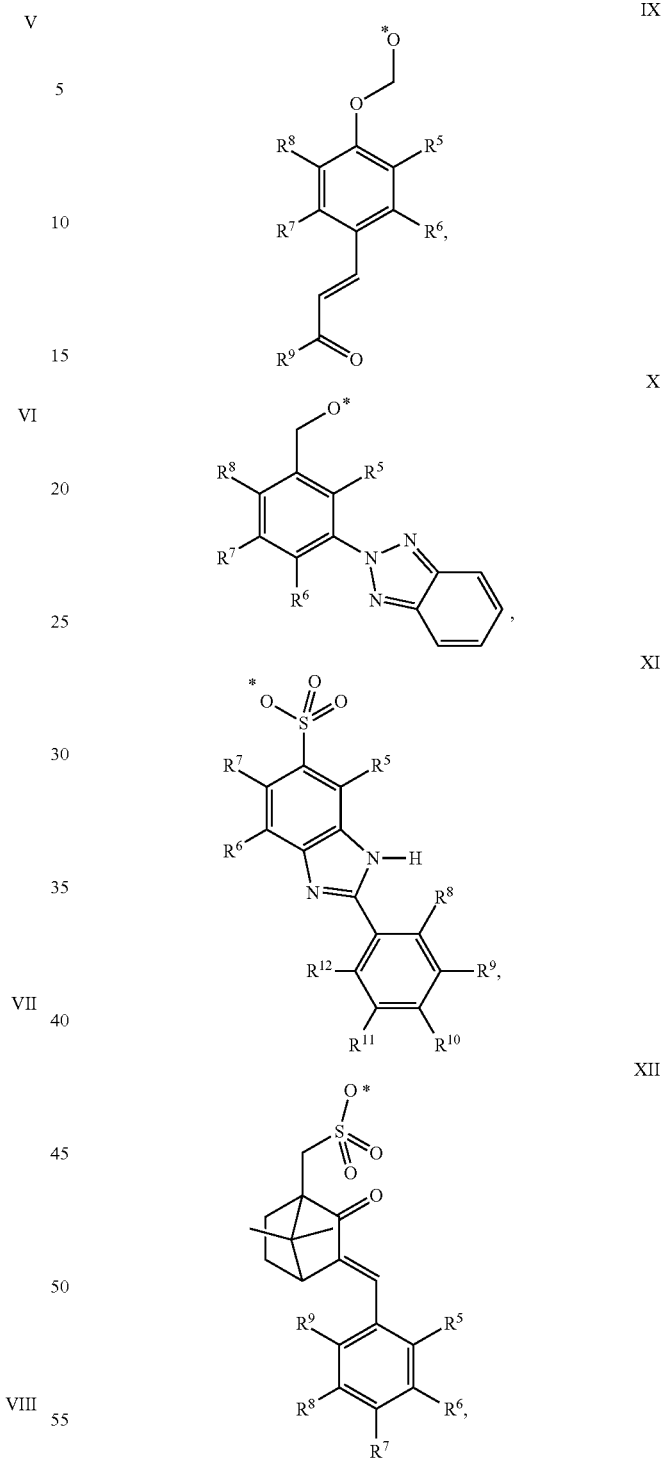
where
$R^5$ to $R^{16}$ each, independently of one another, denote H, —OH, —OA, -A, —$NH_2$, —NHA, —$NA_2$, —NH—($CH_2$—$CH_2$—O)$_n$—H, —N[($CH_2$—$CH_2$—O)$_n$—H]$_2$, —[$NHA_2$]X, —[$NA_3$]X, —$SO_3$H, —[$SO_3$]X or 2H-benzotriazol-2-yl and A is alkyl having 1 to 4 C atoms,
n is an integer from 1 to 25,
X is the counterion to the cations [$NHA_2$]$^+$ and [$NA_3$]$^+$ or the anion [$SO_3$]$^-$ and Y and Z are each, independently of one another, -ascorbyl, hydroxyl, —O-2-ethylhexyl, —O-hexyl, —OA or —NH—C(CH$_3$)$_3$,
are likewise suitable for dyeing keratin-containing fibres or may be present in compositions for dyeing keratin-containing fibres, whether for product protection of sensitive constituents of the composition, as direct dye or oxidation dye component. The abbreviations and explanations described for the compounds of the formulae I or II also apply correspondingly to the compounds of the formulae Ia and IIa.

Even without further comments, it is assumed that a person skilled in the art will be able to utilise the above description in the broadest scope. The preferred embodiments and examples should therefore merely be regarded as descriptive disclosure which is absolutely not limiting in any way. The complete disclosure content of all applications and publications mentioned above and below are incorporated into this application by way of reference.

The percent by weight ratios of the individual ingredients in the preparations of the examples expressly belong to the disclosure content of the description and can therefore be utilised as features.

EXAMPLE 1

Three hair fluids (hair rinses) a), b), c) are investigated for their colouring action by application to hair strands (Eurohaar blond). Recipe a) comprises 1% of the UV filter 4-methoxycinnamic acid 6-O-ascorbate. The comparisons used are recipes comprising equimolar amounts of ascorbic acid (0.52% in recipe b)) and ascorbic acid acetonide (0.64% in recipe c)).

4-Methoxycinnamic acid 6-O-ascorbate

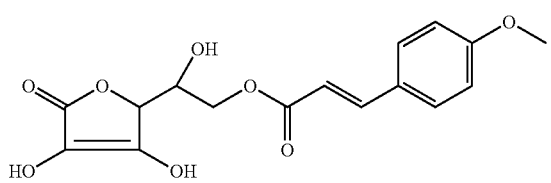 [SMILES: COc1ccc(/C=C/C(=O)OCC(O)C2OC(=O)C(O)=C2O)cc1]

Note: The ascorbic acid acetonide of the following formula was used as comparative substance from the prior art FR2939035:

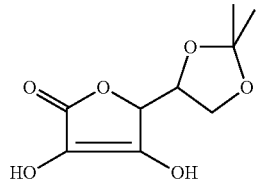

The basic recipe used for a), b), c) comprises the following components:

If ingredients are shown in English, these are INCI names, which are defined in English and are known to the person skilled in the art in the area of cosmetics.

| | Ingredient | Proportion by weight |
|---|---|---|
| Water phase | Sodium Carbomer (Pionier NP37G) | 1% |
| | Ascorbic acid (recipe b)) | 0.52% |
| | Water | to 100% |
| Oil phase | Caprylic/Capric Triglyceride (Miglyol 812) | 7% |
| | Lecitin granules (Emulmetik 300) | 3% |
| | 4-Methoxycinnamic acid 6-O-ascorbate (recipe a)) | 1% |
| | Ascorbic acid acetonide (recipe c)) | 0.64% |

The components of the oil and water phase are in each case combined, the mixtures are warmed on the steam bath (80° C.) and dissolved or melted with stirring. The oil phase is emulsified into the water phase in portions.

Before application of the product, the untreated hair strands are measured chromametrically in the Lab system (=untreated) (evaluation in accordance with CIE-L*a*b, DIN6174). All measurement values are recorded with the aid of a Varian Cary50 spectrophotometer in combination with the Color Analysis software version 3.10 (228). The remission measurement probe used is the Harrick model, Barellino (Serial No BRLVA358431109019, wavelength range 360-830 nm, interval 1 nm, observation angle 2°, illuminant CIED65, baseline correction against white standard (barium sulfate)).

As the next experiment step, 2 ml of hair fluid are in each case applied to a hair strand. The hair strands are subsequently stored at 40° C. for 45 minutes and subsequently rinsed with hair shampoo and blow-dried. This process from product application to the drying step is repeated a total of five times. The second chromametric measurement is subsequently carried out (=after application 5 times). The hair strands are now washed a total of ten times with shampoo in order subsequently to carry out a further chromametric measurement (=after application 5 times+washing 10 times).

Shampoo Constituents:

Lever Faberge, "Organics" brand, 5 natural aroma oils, Happy Hair Days, shampoo, normal hair, batch 20735CO 05:02, *:A.

Ingredients According to Label:

Aqua, Sodium Laureth Sulfate, Cocamidopropyl Betaine, Sodium Chloride, Amodimethicone, Cetrimonium Chloride, Citric Acid, Guar Hydroxypropyltrimonium Chloride, TEA-Dodecylbenzenesulfonate, Carbomer, Mica, Dimethiconol, Trideceth-12, Tocopheryl acetate, Perfume, Isoleucine, Lysine, Sodium Benzoate, CI77891, PPG-9.

Table 1: Measurement Values after Application 5 Times Compared with Untreated Hair Strands:

| | ΔL | Δa | Δb |
|---|---|---|---|
| Recipe a) 1% of 4-methoxycinnamic acid 6-O-ascorbate | −6.59 | 0.68 | −0.36 |
| Recipe b) 0.52% of ascorbic acid | 0.32 | −1.20 | −1.76 |
| Recipe c) 0.64% of ascorbic acid acetonide | 1.88 | −1.25 | −1.21 |

Table 2: Measurement Values after Application 5 Times and Washing with Shampoo 10 Times, as Described Above, Compared with Untreated Hair Strands:

|  | ΔL | Δa | Δb |
|---|---|---|---|
| Recipe a) 1% of 4-methoxycinnamic acid 6-O-ascorbate | −9.29 | 0.24 | −5.42 |
| Recipe b) 0.52% of ascorbic acid | −2.33 | −1.37 | −3.47 |
| Recipe c) 0.64% of ascorbic acid acetonide | 3.01 | −1.38 | −1.62 |

The results show that for recipe a) a very much greater decrease in lightness (hair tinting) is recorded than for the comparative recipes. Indeed, an increase in lightness is observed in the case of c). For recipe a), in addition, very high colour retention or even colour intensification is recorded after washing 10 times. In addition, a maximum Δb blue shift of −5.42 is achieved. By contrast, the tinting value of b) of only 0.32 after application 5 times is very low.

Advantages of the formulations shown below are that they have a very favourable influence on the hair properties, such as hair manageability, combability, smoothness, volume, body, elasticity and sheen.

As described above, the ingredients in English are INCI names, which are defined in English.

EXAMPLE 2

Hair Rinse

|  | Percent by weight [%] |
|---|---|
| Cetearyl Alcohol | 10 |
| Sunflowerseedamidopropyl Ethyldimonium Ethosulfate | 0.5 |
| Ceteareth-20 | 3.0 |
| Panthenol | 0.4 |
| Phenyl Trimethicone | 0.3 |
| Hydroxypropyl Guar Hydroxypropyltrimonium Chloride | 0.8 |
| 4-Methoxycinnamic acid 6-O-ascorbate | 1.0 |
| *Passiflora Incarnata* Seed Oil | 0.2 |
| Basic Red 51 | 0.1 |
| Basic Red 76 | 0.2 |
| Perfume | 1.0 |
| Preservatives | q.s. |
| Citric Acid/Sodium Hydroxide | q.s. to pH 5.5 |
| Aqua | to 100 |

EXAMPLE 3

Hair Rinse

|  | Percent by weight [%] |
|---|---|
| Cetearyl Alcohol | 5.0 |
| Cetrimonium Chloride | 1.0 |
| Polysilicone-15 | 0.5 |
| Panthenol | 0.4 |
| Dimethicone | 0.8 |
| Hydroxypropyl Guar Hydroxypropyltrimonium Chloride | 1.0 |
| 2,4,6-Trimethoxycinnamic acid 6-O-ascorbate | 0.5 |
| 4-Methoxycinnamic acid 6-O-ascorbate | 0.5 |
| Hydrogenated Grapeseed Oil | 1.5 |
| Tiliroside | 0.05 |
| Avocado extract | 0.5 |
| Perfume | 1.0 |
| Preservatives | q.s. |
| Citric Acid/Sodium Hydroxide | q.s. to pH 5.5 |
| Aqua | to 100 |

EXAMPLE 4

Hair Foam

|  | Percent by weight [%] |
|---|---|
| Quaternium-80 | 0.2 |
| Polyquaternium-11 | 0.7 |
| PEG-60 Hydrogenated Castor Oil | 0.5 |
| Perfume | 1.0 |
| Preservatives | q.s. |
| 4-Methoxycinnamic acid 6-O-ascorbate | 0.3 |
| *Passiflora Incarnata* Seed Oil | 0.2 |
| Citric Acid/Sodium Hydroxide | q.s. to pH 4.5 |
| Aqua | to 100 |

The formulation can be employed as leave-on or rinse-off formulation and is packaged in a pressure container as aerosol in the ratio formulation/propellant gas=90/10. Propellant gases which can be employed are, for example, propane or butane or mixtures thereof.

EXAMPLE 5

Shampoo

|  | Percent by weight [%] |
|---|---|
| Sodium Laureth Sulfate | 5.0 |
| Cocamidopropy Betaine | 5.0 |
| Lauroyl Glutamic Acid | 3.0 |
| Decyl Glucoside | 5.0 |
| Polyquaternium-10 | 0.5 |
| PEG-3 Distearate | 0.8 |
| 2,4,6-Trimethoxycinnamic acid 6-O-ascorbate | 0.5 |
| Evening primrose oil | 0.3 |
| Basic Red 51 | 0.1 |
| Ubiquinone | 0.1 |
| Benzyl Alcohol | 0.5 |
| Perfume | 1.0 |
| Preservatives | q.s. |
| Sodium Chloride | 0.8 |
| Citric Acid/Sodium Hydroxide | q.s. to pH 5.5 |
| Aqua | to 100 |

EXAMPLE 6

Shampoo

|  | Percent by weight [%] |
|---|---|
| Palm Kernel/Coco Glucoside | 5.0 |
| Cocamidopropyl Betaine | 6.0 |
| Sodium Laureth Sulfate | 4.0 |
| Guar Hydroxypropyl Trimonium Chloride | 0.5 |

-continued

|  | Percent by weight [%] |
| --- | --- |
| Benzyl Alcohol | 0.5 |
| Hemp seed oil | 0.5 |
| 4-Methoxycinnamic acid 6-O-ascorbate | 0.5 |
| Perfume | 1.0 |
| Preservatives | q.s. |
| Sodium Chloride | 0.8 |
| Lactid Acid/Sodium Hydroxide | q.s. to pH 5.0 |
| Aqua | to 100 |

EXAMPLE 7

Shampoo

|  | Percent by weight [%] |
| --- | --- |
| Sodium Lauryl Glucose Carboxylate | 5.0 |
| Palm Kernel/Coco Glucoside | 5.0 |
| Cocamidopropyl Betaine | 5.0 |
| Polyquaternium-7 | 0.2 |
| 4-Methoxycinnamic acid 6-O-ascorbate | 0.5 |
| Benzyl Alcohol | 0.5 |
| Passiflora Incarnata Seed Oil | 0.5 |
| PEG-60 Hydrogenated Castor Oil | 0.5 |
| PEG-18 Glyceryl Cocoate/Oleate | 1.0 |
| Perfume | 1.0 |
| Preservatives | q.s. |
| Sodium Chloride | 0.8 |
| Lactid Acid/Sodium Hydroxide | q.s. to pH 6.0 |
| Aqua | to 100 |

EXAMPLE 8

Hair Dyeing Recipes

|  | 1 | 2 | 3 | 4 | 5 | 6 | 7 |
| --- | --- | --- | --- | --- | --- | --- | --- |
| Benzyl Alcohol | 2.5 | | | | | | |
| Propylene Carbonate | 10 | | | | | | |
| Ethanol | 5.0 | | | | | | |
| Hydroxyethylcellulose | 2.0 | | | | | | |
| Pirenoxine sodium CAS 51410-30-1 | 2.0 | | | | | 2.0 | |
| Tramsanguine CAS 34083-17-5 | | 1.0 | | | | 1.0 | |
| Cinnabarine CAS 606-59-7 | | | 1.0 | | | | |
| Cinnabaric acid CAS 146-90-7 | | | | 1.0 | | | |
| Resorcinol Blue CAS 71939-12-3 | | | | | 1.0 | | |
| 4-Methoxycinnamic acid 6-O-ascorbate | 1.0 | 1.0 | 2.0 | 1.0 | 1.0 | 0.5 | |
| 2,4,6-Trimethoxy-cinnamic acid 6-O-ascorbate | | | | | | 1.5 | 2.0 |
| Perfume | 1.0 | 1.0 | 1.0 | 1.0 | 1.0 | 1.0 | 1.0 |
| Preservatives | q.s. | q.s. | q.s. | q.s. | q.s. | q.s. | q.s. |
| Citric Acid | q.s. to pH 5.5 | q.s. to pH 5.5 | q.s. to pH 5.5 | q.s. to pH 5.5 | q.s. to pH 5.5 | q.s. to pH 5.5 | q.s. to pH 5.5 |
| Aqua | to 100 | to 100 | to 100 | to 100 | to 100 | to 100 | to 100 |

EXAMPLE 9

Use for Intensive Tinting (Developer Comprising 4-methoxycinnamic acid 6-O-ascorbate Instead of Hydrogen Peroxide)

For intensive tinting of blond hair strands (Eurohaar), a commercially available tinting care cream is divided into three, and in each case 11 g are mixed with 10 ml of developer A (=3% $H_2O_2$ solution, pH=4-5), 10 ml of developer B (commercial developer emulsion see below) and 10 ml of developer C (=1% solution of 4-methoxycinnamic acid 6-O-ascorbate in citrate buffer pH6/ethanol=80/20). The respective mixtures are homogenised by shaking under air. After 1 h, in each case 1.5 ml of the homogenised mixture are brushed uniformly onto a hair strand (about 250 mg of hair). The mixture is left at 40° C. for 30 min, and the hair is subsequently rinsed with lukewarm water. The hair is blow-dried at a temperature of about 60° C.

Ingredients of the tinting care cream: Aqua, Cetearyl Alcohol, Ethanolamine, Sodium Laureth Sulfate, Cocamidopropyl Betaine, Coconut Alcohol, Toluene-2,5-Diamine Sulfate, Polyquaternium-22, Ceteareth-20, Sodium Chloride, 2-Methylresorcinol, Disodium Cocoamphodipropionate, Sodium Sulfite, Ascorbic Acid, Macademia Ternifolia Seed Oil, Sodium Silicate, 4-chlororesorcinol, Perfume, Etidronic Acid, 2-Amino-3-Hydroxypyridine, Resorcinol, 2-Amino-6-Chloro-4-Nitrophenol, m-Aminophenol, Methyl Alcohol.

Ingredients of developer B: Aqua, Hydrogen peroxide, Acrylates Copolymer, Etidronic Acid, Sodium Laureth Sulfate, 2,6-Dicarboxypyridine, Disodium Pyrophosphate, Dimethicone The following colour coordinates were obtained for the various batches:

|  | L* | a* | b* |
| --- | --- | --- | --- |
| Developer A | −33.1 | 1.66 | −13.1 |
| Developer B | −32.4 | 2.36 | −12.6 |
| Developer C | −31.6 | 6.10 | −5.64 |

Besides the replacement of hydrogen peroxide by 4-methoxycinnamic acid 6-O-ascorbate, it is furthermore also possible to use mixtures of these two components. Furthermore, the ascorbic acid derivatives of the formula I or II, as described above or described as preferred, can also be combined directly with ingredients of the tinting care cream or developer emulsion described in this example.

The invention claimed is:

1. A method for dyeing keratin-containing fiber comprising applying to the keratin-containing fiber a composition comprising at least one compound of the formula I or II or a salt thereof:

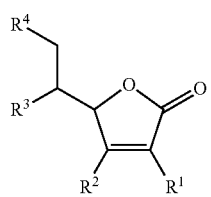

I

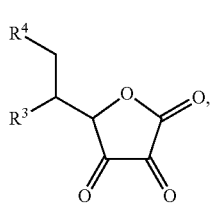

wherein
- $R^1$ or $R^2$ each, independently of one another, denote hydroxyl, —O-alkyl, —OC(O)-alkyl, —PO$_3$M or —O-glycosyl,
- alkyl denotes a straight-chain or branched alkyl group having 1 to 10 C atoms,
- M denotes an alkali or alkaline-earth metal cation or H,
- $R^3$ or $R^4$ each, independently of one another, stand for hydroxyl or a group of the formula III, with the proviso that at least one of the radicals $R^3$ or $R^4$ is of the formula III:

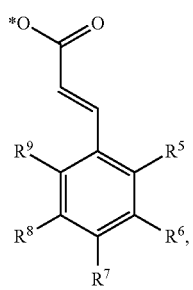

where
- * indicates the point of attachment of the formula III group,
- $R^5$ to $R^9$ each, independently of one another, denote H, —OH, a straight-chain or branched alkoxy group having 1 to 20 C atoms, a fluorinated straight-chain or branched alkoxy group having 1 to 20 C atoms, -A, —NH$_2$, —NHA, —NA$_2$, —NH—(CH$_2$—CH$_2$—O)$_n$—H, —N[(CH$_2$—CH$_2$—O)$_n$—H]$_2$, —[NHA$_2$]X, —[NA$_3$]X, —SO$_3$H, —[SO$_3$]X, 2H-benzotriazol-2-yl or —OC(O)-alkyl,
- A denotes a straight-chain or branched alkyl group having 1 to 20 C atoms and
- X is the counterion to the cations [NHA$_2$]$^+$ and [NA$_3$]$^+$ or the anion [SO$_3$]$^-$.

2. The method of claim 1, wherein the substituents $R^5$ to $R^9$ in the compounds of the formula I or II each, independently of one another, denote H, straight-chain or branched alkoxy group having 1 to 20 C atoms, fluorinated straight-chain or branched alkoxy group having 1 to 20 C atoms or —OC(O)-alkyl.

3. The method of claim 1, wherein at least one of the substituents $R^5$ to $R^9$ in the compounds of the formula I or II stands for a straight-chain or branched alkoxy group having 1 to 20 C atoms.

4. The method of claim 1, wherein the keratin-containing fiber is selected from human hair, wool, animal pelts or feathers.

5. The method of claim 1, wherein the composition is applied to the keratin-containing fiber at least once daily or at least two times successively, left on the fiber for a period of time and subsequently rinsed out or washed out using a shampoo.

6. The method of claim 5, wherein the composition is left on the fiber after applying for 20 to 45 minutes before rinsing or washing out.

7. The method of claim 5, wherein the keratin-containing fiber is pretreated with a pretreatment agent before applying the composition.

8. The method of claim 5, wherein composition is applied and rinsed out or washed out at least two times in a day.

9. The method of claim 1, wherein the at least one compound of the formula I or II or a salt thereof further stabilizes the dyed color of the keratin fiber and/or stabilizes other dye molecules additionally used for dyeing the keratin fiber.

10. The method of claim 1, wherein an oxidation dye is further applied to the keratin fiber for dyeing the keratin fiber.

11. The method of claim 1, wherein the dyeing of keratin fiber results in tinting, bleaching, oxidative dyeing, semipermanent dyeing, permanent dyeing or temporary dyeing of the keratin fiber.

12. The method of claim 1, wherein the composition comprises at least one of the following compounds of formula I: 4-methoxycinnamic acid 6-O-ascorbate; 2,4-dimethoxycinnamic acid 6-O-ascorbate; 2,4,6-trimethoxycinnamic acid 6-O-ascorbate; or 2,3,4-trimethoxycinnamic acid 6-O-ascorbate, 2,4,5-trimethoxycinnamic acid 6-O-ascorbate.

13. The method of claim 1, wherein the composition comprises the compound(s) of the formula I and/or II or salt thereof, in an amount above 0.01% by weight and below 10% by weight, based on the entire composition.

14. The method of claim 1, wherein the composition comprises the compound(s) of the formula I and/or II or salt thereof, in an amount of from 0.05 to 5% by weight.

15. The method of claim 1, wherein the composition is in the form of a kit having one, two or three components, whereby, when the kit has two or three components, the components are mixed before or during applying to the kertain fiber.

* * * * *